US008735314B2

(12) United States Patent
Nagaki et al.

(10) Patent No.: US 8,735,314 B2
(45) Date of Patent: *May 27, 2014

(54) CATALYSTS FOR PRODUCING ACRYLIC ACIDS AND ACRYLATES

(75) Inventors: Dick Nagaki, The Woodlands, TX (US); Craig Peterson, Houston, TX (US); Mark Scates, Houston, TX (US); Heiko Weiner, Pasadena, TX (US); Josefina T. Chapman, Houston, TX (US); Alexandra S. Locke, West Valley City, UT (US)

(73) Assignee: Celanese International Corporation, Dallas, TX (US)

( * ) Notice: Subject to any disclaimer, the term of this patent is extended or adjusted under 35 U.S.C. 154(b) by 274 days.

This patent is subject to a terminal disclaimer.

(21) Appl. No.: 13/248,710

(22) Filed: Sep. 29, 2011

(65) Prior Publication Data

US 2013/0085293 A1    Apr. 4, 2013

(51) Int. Cl.
| B01J 31/00 | (2006.01) |
| B01J 27/00 | (2006.01) |
| B01J 27/198 | (2006.01) |
| B01J 23/00 | (2006.01) |
| C07B 35/00 | (2006.01) |
| C07C 51/00 | (2006.01) |
| C07C 51/42 | (2006.01) |

(52) U.S. Cl.
USPC ........... 502/150; 502/158; 502/172; 502/208; 502/209; 502/350; 502/353; 562/599; 562/600

(58) Field of Classification Search
USPC ......... 502/150, 172, 158, 208, 209, 350, 353; 562/599, 600
See application file for complete search history.

(56) References Cited

U.S. PATENT DOCUMENTS

| 3,464,930 | A | * | 9/1969 | Goehre et al. ................ 502/309 |
| 3,948,807 | A | | 4/1976 | Fuchigami et al. |
| 4,994,608 | A | | 2/1991 | Torrence et al. |
| 5,001,259 | A | | 3/1991 | Smith et al. |
| 5,026,908 | A | | 6/1991 | Smith et al. |
| 5,144,068 | A | | 9/1992 | Smith et al. |
| 5,364,824 | A | | 11/1994 | Andrews et al. |
| RE35,377 | E | | 11/1996 | Steinberg et al. |
| 5,599,976 | A | | 2/1997 | Scates et al. |
| 5,821,111 | A | | 10/1998 | Grady et al. |
| 6,143,930 | A | | 11/2000 | Singh et al. |
| 6,232,352 | B1 | | 5/2001 | Vidalin |
| 6,627,770 | B1 | | 9/2003 | Cheung et al. |
| 6,657,078 | B2 | | 12/2003 | Scates et al. |
| 6,685,754 | B2 | | 2/2004 | Kindig et al. |
| 7,005,541 | B2 | | 2/2006 | Cheung et al. |
| 7,115,772 | B2 | | 10/2006 | Picard et al. |
| 7,208,624 | B2 | | 4/2007 | Scates et al. |
| 7,569,508 | B2 | * | 8/2009 | Zhou et al. ................ 502/150 |
| 8,501,652 | B2 | * | 8/2013 | Johnston et al. ............. 502/100 |
| 8,507,721 | B2 | * | 8/2013 | Herzog et al. ................ 562/599 |
| 2006/0039843 | A1 | | 2/2006 | Patchett et al. |
| 2010/0197959 | A1 | * | 8/2010 | Johnston et al. ............. 560/265 |
| 2012/0071688 | A1 | | 3/2012 | Herzog et al. |
| 2012/0277466 | A1 | * | 11/2012 | Nagaki et al. ................ 562/599 |
| 2012/0289743 | A1 | * | 11/2012 | Nagaki et al. ................ 562/599 |
| 2013/0053599 | A1 | * | 2/2013 | Weiner et al. ................ 560/211 |
| 2013/0085293 | A1 | * | 4/2013 | Nagaki et al. ................ 562/599 |
| 2013/0245311 | A1 | * | 9/2013 | Nagaki et al. ................ 560/211 |
| 2013/0245312 | A1 | * | 9/2013 | Nagaki et al. ................ 560/214 |
| 2013/0317254 | A1 | * | 11/2013 | Kotsianis et al. ............. 562/599 |

FOREIGN PATENT DOCUMENTS

| WO | WO 2008/071640 | | 6/2008 | |
| WO | 2012/148837 | * | 11/2012 | ............. B01J 23/22 |
| WO | 2013/048692 | * | 4/2013 | ............. B01J 23/22 |

OTHER PUBLICATIONS

M. Ai, J. Catal., 107, 201, (1987).
M. Ai., J. Catal., 124, 293, (1990).
M. Ai., Appl. Catal., 36, 221, (1988).
M. Ai., Shokubai, 29, 522, (1987).
M. Ai, J. Catal., 113, (1998).
M. Ai, Appl. Catal., 48, (1989).
Bosman, et al., J. Catalysis, vol. 148, (1994), p. 660.
Monros, et al., J. Materials Science, vol. 28, (1993), p. 5832.
Jubb & Bowen, J. Material Science, vol. 22, (1987), pp. 1963-1970.
Iler R.K., The Chemistry of Silica, (Wiley, New York, 1979).
Brinker C J & Scherer G W, Sol-Gel Science, Academic Press (1990).
International Search Report and Written Opinion mailed Apr. 25, 2013 in corresponding International Application No. PCT/US2012/054077.

* cited by examiner

Primary Examiner — Patricia L Hailey

(57) ABSTRACT

In one embodiment, the invention is to a catalyst composition comprising vanadium and titanium. The catalyst composition further comprises ethylene glycol and citric acid. Preferably, the catalyst composition is substantially free of oxalic acid and lactic acid.

43 Claims, No Drawings

CATALYSTS FOR PRODUCING ACRYLIC ACIDS AND ACRYLATES

FIELD OF THE INVENTION

The present invention relates generally to the production of acrylic acid. More specifically, the present invention relates to catalysts used in the production of acrylic acid via the condensation of acetic acid and formaldehyde.

BACKGROUND OF THE INVENTION

α,β-unsaturated acids, particularly acrylic acid and methacrylic acid, and the ester derivatives thereof are useful organic compounds in the chemical industry. These acids and esters are known to readily polymerize or co-polymerize to form homopolymers or copolymers. Often the polymerized acids are useful in applications such as superabsorbents, dispersants, flocculants, and thickeners. The polymerized ester derivatives are used in coatings (including latex paints), textiles, adhesives, plastics, fibers, and synthetic resins.

Because acrylic acid and its esters have long been valued commercially, many methods of production have been developed. One exemplary acrylic acid ester production process utilizes the reaction of acetylene with water and carbon monoxide or the reaction of an alcohol and carbon monoxide to yield the acrylate ester. Another conventional process involves the reaction of ketene (often obtained by the pyrolysis of acetone or acetic acid) with formaldehyde. These processes have become obsolete for economic, environmental, or other reasons.

Another acrylic acid production method utilizes the condensation of formaldehyde and acetic acid and/or carboxylic acid esters. This reaction is often conducted over a catalyst. For example, condensation catalysts consisting of mixed oxides of vanadium and phosphorus were investigated and described in M. Ai, *J. Catal.*, 107, 201 (1987); M. Ai, *J. Catal.*, 124, 293 (1990); M. Ai, *Appl. Catal.*, 36, 221 (1988); and M. Ai, Shokubai, 29, 522 (1987). Also, M. Ai, *J. Catal.*, 113, (1988) and M. Ai, *Appl. Catal.*, 48, (1989) discuss the use of some organic compounds in the preparation of vanadium/titanium binary phosphate catalysts.

Thus, the need exists for improved processes for producing acrylic acid, and for improved catalysts capable of providing high acetic acid conversions in the formation of acrylic acid.

SUMMARY OF THE INVENTION

In one embodiment, the invention is to a catalyst composition comprising and active phase comprising vanadium and titanium. The active phase of the catalyst composition may further comprise ethylene glycol and citric acid. The citric acid may be present in an amount ranging from 0.01 wt % to 10 wt %. Preferably, the catalyst composition is prepared using substantially no oxalic acid and lactic acid, e.g., no oxalic acid and lactic acid. As a result, the catalyst composition is substantially free of oxalic acid and lactic acid. In one embodiment, the catalyst composition has a surface area of at least 13.5 m$^2$/g, e.g., at least 15 m$^2$/g or at least 20 m$^2$/g. In one embodiment, the catalyst composition comprises a plurality of pores and the plurality of pores, collectively, has a pore diameter of less than 17.4 nm, e.g., less than 16.5 nm or less than 10 nm. In some embodiments, the inventive catalyst composition further comprises a reducing agent.

In another embodiment, the present invention is to a process for producing the above-mentioned catalyst composition. The process comprises the step of contacting a titanium precursor, a vanadium precursor, phosphoric acid, citric acid, and optionally a reducing agent to form a catalyst precursor mixture. Preferably, the catalyst precursor mixture is prepared using substantially no oxalic acid and lactic acid. As a result, the catalyst precursor mixture is substantially free of oxalic acid and lactic acid. The process further comprises the step of drying the catalyst precursor mixture to form the catalyst composition.

In another embodiment, the present invention is to a process for producing acrylic acid. The process comprises the step of contacting acetic acid and an alkylenating agent over the inventive catalyst under conditions effective to produce acrylic acid and/or acrylate.

DETAILED DESCRIPTION OF THE INVENTION

Introduction

Production of unsaturated carboxylic acids such as acrylic acid and methacrylic acid and the ester derivatives thereof via most conventional processes have been limited by economic and environmental constraints. One process for producing these acids and esters involves the aldol condensation of formaldehyde and (i) acetic acid and/or (ii) ethyl acetate over a catalyst. Exemplary classes of conventional catalysts for this reaction include binary vanadium-titanium phosphates, vanadium-silica-phosphates, and alkali metal-promoted silicas, e.g., cesium- or potassium-promoted silicas. The alkali metal-promoted silicas, however, have been known to exhibit only low to moderate activity when used in aldol condensation reactions. As a result, the alkali metal-promoted silicas typically require metal dopants, e.g., bismuth, lanthanum, lead, thallium, and tungsten, to improve catalyst performance.

Binary vanadium-titanium phosphates have been studied with regard to the condensation of acetic acid and formaldehyde (or a methanol/oxygen mixture) to form acrylic acid. Catalysts with a vanadium:titanium:phosphorus molar ratio of 1:2:x, where x is varied from 4.0 to 7.0, have traditionally shown that the catalyst activity decreases steadily as the phosphorus content increased (see, for example M. Ai, *J. Catal.*, 107, 201 (1987); M. Ai, *J. Catal.*, 124, 293 (1990); M. Ai, *Appl. Catal.*, 36, 221 (1988); and M. Ai, Shokubai, 29, 522 (1987), discussed above). The highest selectivity with respect to the aldol condensation products, e.g., acrylic acid and methyl acrylate, was obtained where x was 6.0. Further, with these catalysts, the molar ratio of vanadium to titanium was maintained at or below 1:2.

Vanadyl pyrophosphate (($VO)_2P_2O_7$) catalysts have also been extensively studied. In particular, vanadyl pyrophosphates in combination with other phosphates, i.e., titanium pyrophosphate ($TiP_2O_7$), have been investigated and have shown significant catalytic activity in the condensation of carboxylic acids and esters with formaldehyde. Several studies have shown that vanadium-titanium-phosphorus ternary oxides may demonstrate good catalytic performance in the aldol condensation of acetic acid with methanol/formaldehyde. In comparison, $TiO_2$, $V_2O_5$—$TiO_2$, and $TiO_2$—$P_2O_5$ were not found to be as effective. The best performance of these combinations of $(VO)_2P_2O_7$ and $TiP_2O_7$, however, has been obtained with a $(VO)_2P_2O_7$:$TiP_2O_7$ molar ratio of 1:4. At the $(VO)_2P_2O_7$:$TiP_2O_7$ molar ratio of 1:4, the molar ratio of vanadium:titanium:phosphorus in the resulting composition is 1:2:5. Thus, the $(VO)_2P_2O_7$/$TiP_2O_7$ catalyst systems that provided the highest yields (under the respective reaction conditions) were those having a vanadium to titanium ratio of about 0.5:1.

Also, M. Ai, *J. Catal.*, 113, (1988) and M. Ai, *Appl. Catal.*, 48, (1989) discuss the use of organic compounds in the preparation of vanadium-titanium binary phosphate catalyst. The methods discussed in these documents employ various organic compounds in the preparation of a vanadium precursor. The vanadium precursor is used to prepare the final catalyst composition. In M. Ai, *J. Catal.*, 113, (1988), however, oxalic acid is used along with the various organic compounds to prepare of the vanadium precursor. Catalyst preparation without the use of oxalic acid is not contemplated or suggested and this document fails to teach any benefit of eliminating or replacing oxalic acid in the preparation of the vanadium precursor. In M. Ai, *Appl. Catal.*, 48, (1989), various organic compounds are listed for use in the preparation of the vanadium precursor. Although other organic compounds are listed, this document focuses on the use of lactic acid. This document concludes that the use of lactic acid induces increases in surface area. The document further concludes, however, that the role of hydroxycarboxylic acids, generally, is unclear and that correlations between the surface area and catalyst preparation methods are difficult to draw. Importantly, these documents fail to teach that citric acid should be used as the organic compound in the absence of other organic compounds, e.g., oxalic acid, lactic acid, hydrochloric acid, or 2-propanol or replace at least a portion of the conventional oxalic acid and/or lactic acid.

Catalyst Composition

In one embodiment, the present invention is to a catalyst composition comprising an active phase comprising vanadium and titanium, and optionally phosphorus. It has now been discovered that the use of citric acid in combination with the elimination or reduction of oxalic acid and/or lactic acid, which are conventionally used, e.g., as solvents, in the preparation of vanadium-titanium-phosphate catalyst compositions, surprisingly and unexpectedly yield a catalyst composition that, when used in an aldol condensation of alkylenating agent and an alkanoic acid form acrylic acid and/or other acrylate products, provides for significant improvement in reaction efficiencies. Conventionally, the oxalic acid and/or lactic acid are used, e.g., as a solvent, in the preparation of a vanadium precursor mixture and the vanadium precursor is contacted with a titanium precursor to form a catalyst precursor mixture. In preferred embodiments, the replacement of at least portion of the oxalic acid and/or lactic acid that is conventionally used, with citric acid surprisingly provides for a catalyst that provides for an increase in alkanoic acid conversion along with an increase in alkanoic acid selectivity.

As used herein, in one embodiment, the term "substantially free of oxalic acid and lactic acid" means that oxalic acid and/or lactic acid are present, if at all, in very small amounts, e.g., less than 1000 wppm, less than 500 wppm, or less than 100 wppm. In one embodiment, the term "substantially free of oxalic acid and lactic acid" means the oxalic acid and lactic acid are not present.

Without being bound by theory, it is believed that of the use of citric acid in the preparation of the catalyst composition may inter alia 1) improve dispersion of V and Ti throughout the catalyst composition; and/or 2) increase the $V^{4+}/V^{5+}$ ratio in the catalyst composition.

In some embodiments, the active phase of the catalyst composition may comprise a detectable amount of citric acid along with the titanium and the vanadium. Preferably, the active phase further comprises a detectable amount of ethylene glycol. As such, in some embodiments, the resultant active phase may comprise from 0.01 wt % to 10 wt % citric acid, e.g., from 0.1 wt % to 5 wt % or from 1 wt % to 3 wt %.

In terms of lower limits, the resultant active phase may comprise at least 0.01 wt % citric acid, e.g., at least 0.1 wt % or at least 1.0 wt %. In terms of upper limits, the resultant active phase may comprise less than 10 wt % citric acid, e.g., less than 5 wt % or less than 1 wt %. In some embodiments, the resultant active phase may comprise from 0.01 wt % to 10 wt % ethylene glycol, e.g., from 0.1 wt % to 5 wt % or from 1 wt % to 3 wt %. In terms of lower limits, the resultant active phase may comprise at least 0.01 wt % ethylene glycol, e.g., at least 0.1 wt % or at least 1.0 wt %. In terms of upper limits, the resultant active phase may comprise less than 10 wt % ethylene glycol, e.g., less than 5 wt % or less than 1 wt %. Preferably, these limits and ranges apply to an active phase of the catalyst composition. The active phase is the portion of the catalyst composition comprising the components that promote the catalysis.

In other embodiments, the citric acid and/or the ethylene glycol is disintegrated, evaporated from the resultant catalyst composition, and/or burned off the resultant catalyst composition, e.g., in a drying step. As a result, little or no citric acid and/or ethylene glycol remains in the resultant catalyst composition. Without being bound by theory, in these embodiments, even though these components may not remain in the resultant catalyst, the effects of these components may be evident in the physical and/or chemical characteristics of the catalyst composition, e.g., surface area and/or pore size.

Regardless of whether an amount of the citric acid and/or the ethylene glycol remains in the resultant catalyst composition, the inventive catalyst composition, in some embodiments has pores and the pores, collectively, have an average pore diameter ranging from 1.0 nm to 17.4 nm, e.g., 5.0 nm to 15 nm, from 5.0 nm to 10.0 nm, from 7.0 nm to 15.0 nm or from 7.0 nm to 10.0 nm. In terms of limits, the pores of the catalyst composition may have an average pore diameter of less than 17.4 nm, e.g., less than 15 nm or less than 10 nm. Such an average pore diameter is significantly less than that of a similar catalyst composition formed from similar starting materials, but without employing the citric acid. In one embodiment, the catalyst composition has a higher surface area than a similar catalyst composition formed from a similar process and starting materials, but which also utilizes oxalic acid and lactic acid in the preparation of the vanadium precursor, e.g., at least 30% higher, 40% higher, 50% higher or at least 60% higher. For example, in one embodiment, the catalyst composition has a surface area of at least 13.5 m$^2$/g, e.g., at least 15 m$^2$/g or at least 20 m$^2$/g, as determined by BET measurements. In terms of ranges, the surface area may range from 13.5 m$^2$/g to 100 m$^2$/g, e.g., from 15 m$^2$/g to 80 m$^2$/g or from 20 m$^2$/g to 60 m$^2$/g, as determined by BET measurements. As one comparative example, a catalyst composition prepared using only oxalic acid and lactic acid as a solvent in the preparation of the vanadium precursor yielded a catalyst composition having a surface area of 0.6 m$^2$/g.

It has now been found that the inventive catalyst compositions comprising vanadium, titanium, and citric acid and optionally ethylene glycol, that are prepared without using oxalic acid and lactic acid as a solvent surprisingly and unexpectedly achieve high alkanoic acid, e.g., acetic acid, conversions when utilized in, for example, aldol condensation reactions of alkanoic acid(s) and alkylenating agents. For example, depending on the temperature at which the alkanoic acid formation reaction is conducted, alkanoic acid conversions of at least 10 mol %, e.g., at least 20 mol %, at least 30 mol %, at least 40 mol %, or at least 50 mol.%, may be achieved with the inventive catalyst compositions. This increase in alkanoic acid conversion is achieved while maintaining selectivity to the desired acrylates, e.g., acrylic acid and/or methyl acrylate. In one embodiment, selectivity to the desired acrylates is increases, e.g., by at least 10% or at least 20%. For example, selectivities to the desired acrylate (optionally acrylic acid and/or methyl acrylate) of at least 50 mol %, e.g., at least 60 mol %, at least 65 mol %, at least 70 mol %, or at least 75 mol %, may be achieved with the catalyst of the present invention. As a result, acrylate space time yield is improved, e.g., by at least 30%, at least 40% or at least 50% over comparable catalysts formed using conventional amounts of oxalic acid and lactic acid and optionally without citric acid and/or ethylene glycol. Conventionally, higher conversions and higher selectivities are believed to be achieved by catalyst compositions having high surface areas and larger pore diameters. Surprisingly and unexpectedly, the inventive catalyst compositions, which have the pore diameters discussed above, are capable of achieving improved acetic acid conversions and acrylate product selectivities and yields.

The total amounts of vanadium and titanium in the catalyst compositions, e.g., in the active phase of the catalyst compositions, of the invention may vary widely. In some embodiments, for example, the catalyst comprises at least 1 wt % vanadium, e.g., at least 8 wt % or at least 13 wt %, based on the total weight of the active phase. The catalyst composition may comprise at least 5 wt % titanium, e.g., at least 10 wt % or at least 12 wt %. In terms of ranges, the catalyst composition may comprise from 1 wt % to 40 wt % vanadium, e.g., from 1 wt % to 30 wt %, from 8 wt % to 17 wt % or from 13 wt % to 16 wt % vanadium; and from 5 wt % to 40 wt % titanium, e.g., from 5 wt % to 15 wt %, from 10 wt % to 16 wt % or from 10 wt % to 13 wt % titanium. The catalyst composition preferably comprises vanadium and titanium, in combination, in an amount greater than 20 wt %, e.g., greater than 25 wt % or greater than 35 wt %. In terms of ranges, the combined weight percentage of the vanadium and titanium components may range from 6 wt % to 80 wt %, e.g., from 25 wt % to 60 wt % or from 30 wt % to 50 wt %. In one embodiment, the molar ratio of vanadium to titanium in the active phase of the catalyst composition may be greater than 0.5:1, e.g., greater than 0.75:1, greater than 1:1, or greater than 1.25:1. In terms of ranges, the molar ratio of vanadium to titanium in the inventive catalyst composition may range from 0.5:1 to 20:1, e.g., from 0.5:1 to 10:1, or from 1:1 to 10:1.

In other embodiments, the inventive catalyst composition may further comprise other compounds or elements (metals and/or non-metals). For example, the catalyst composition may further comprise phosphorus and/or oxygen. In these cases, the catalyst composition may comprise from 15 wt % to 45 wt % phosphorus, e.g., from 20 wt % to 35 wt % or from 23 wt % to 27 wt %; and/or from 30 wt % to 75 wt % oxygen, e.g., from 35 wt % to 65 wt % or from 48 wt % to 51 wt %.

In one embodiment, a molar ratio of citric acid to the combination of vanadium and titanium in the active phase of the catalyst ranges from 0.01:1 to 10:1, e.g., from 0.05:1 to 1:0.05 or from 0.1:1 to 1:0.1. In one embodiment, a molar ratio of citric acid to vanadium in the active phase of the catalyst ranges from 0.01:1 to 10:1, e.g., from 0.05:1 to 1:0.05 or from 0.1:1 to 1:0.1. In one embodiment, a molar ratio of citric acid to titanium in the active phase of the catalyst ranges from 0.01:1 to 10:1, e.g., from 0.05:1 to 1:0.05 or from 0.1:1 to 1:0.1.

In some embodiments, at least some of the titanium is present in compound form such as in the form of titanium dioxide. For example, the catalyst composition may comprise titanium dioxide in an amount ranging from 0.1 wt % to 95 wt %, e.g., from 5 wt % to 50 wt % or from 7 wt % to 25 wt %. Some of the titanium dioxide, in some cases, may be in the rutile and/or anatase form, however, this amount of rutile and/or anatase titanium dioxide advantageously may be reduced as a result of the addition of the oxide additive. Preferably less than 20 wt % of the titanium dioxide, if present in the catalyst, is in rutile form, e.g., less than 10 wt %, less than 5 wt %, less than 1 wt %, or less than 0.1 wt %. It is contemplated, however, that the catalyst composition, in some embodiments, may comprise a minor amount of rutile titanium dioxide in an amount of at least 5 wt %, e.g., at least 10 wt % or at least 20 wt %. In one embodiment, less than 20 wt % of the titanium dioxide, if present in the catalyst composition, is in anatase form, e.g., less than 10 wt %, less than 5 wt %, less than 1 wt %, or less than 0.1 wt %. It is contemplated, however, that the catalyst composition, in some embodiments, may comprise a minor amount of anatase titanium dioxide in an amount of at least 5 wt %, e.g., at least 10 wt % or at least 20 wt %.

In another embodiment, the titanium is present in the form of amorphous titanium hydroxide gel, which is preferably converted to $TiP_2O_7$. The titanium hydroxide gel may be prepared by any suitable means including, but not limited to, the hydrolysis of titanium alkoxides, substituted titanium alkoxides, or titanium halides. In other embodiments, colloidal titania sols and/or dispersions may be employed. In one embodiment, titania coated colloidal particles or supports are used as a source of titanium dioxide. The hydrous titania may be amorphous or may contain portions of anatase and/or rutile depending on preparation method and heat treatment.

Upon treatment with a phosphating agent, the various forms of titania may be converted to titanium phosphates and/or titanium pyrophosphates. In some cases, a portion of the titanium may be present as unconverted titania and, hence, will be present in the final catalyst as amorphous, anatase, and/or rutile forms.

Generally speaking, the proportion of the crystalline forms of titania present in the catalyst is dependent on the titanium precursor, the preparative method, and/or the post-phosphorylating treatment. In one embodiment, the amount of anatase and rutile present in the active phase of the catalyst is minimized. The amount of crystalline titania, however, may be high with only a thin shell of porous catalyst existing on the titania support.

In one embodiment, in the production of the catalyst composition, a pentavalent vanadium compound is reduced. The reduced pentavalent compound may be combined with a phosphorus compound and, optionally, promoters under conditions effective to provide or maintain the vanadium in a valence state below +5 to form the active metal phosphate catalysts.

In one embodiment, suitable vanadium compounds that serve as a source of vanadium in the catalyst contain pentavalent vanadium and include, but are not limited to, vanadium pentoxide or vanadium salts such as ammonium metavanadate, vanadium oxytrihalides, vanadium alkylcarboxylates, vanadium tetraoxide, vanadium oxysulfate, oxyvanadium carboxylate salt, vanadium oxyacetylacetonate complex, or vanadic acid and mixtures thereof In one embodiment, suitable phosphorus compounds that serve as a source of phosphorus in the catalyst contain pentavalent phosphorus and include, but are not limited to, phosphoric acid, ammonium phosphates, phosphorus pentoxide, polyphosphoric acid, or phosphorus perhalides such as phosphorus pentachloride, and mixtures thereof Preferably, the active phase of the catalyst corresponds to the formula

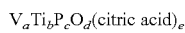

wherein the letters a, b, c, d, and e are the relative molar amounts (relative to 1.0) of vanadium, titanium, phosphorus, oxygen, and citric acid, respectively, in the catalyst. In these embodiments, the ratio of e to b is preferably greater than 0.05:1, e.g., greater than 0.1:1, greater than 0.5:1, or greater than 1:1. Preferred ranges for molar variables a, b, c, d, and e are shown in Table 1. In some embodiments, the ratio of a to b is greater than 0.5:1, e.g., greater than 0.75:1, greater than 1:1, or greater than 1.25:1. In some embodiments, the active phase of the catalyst may comprise of little or no citric acid. Preferred ranges for molar variables a, b, c, d, and e are shown in Table 1.

TABLE 1

Molar Ranges

| | Molar Range | Molar Range | Molar Range |
|---|---|---|---|
| a | 1 to 8 | 2 to 6 | 2 to 5 |
| b | 4 to 8 | 4 to 7 | 4 to 6 |
| c | 10 to 30 | 20 to 28 | 23 to 26 |
| d | 30 to 70 | 30 to 60 | 37 to 58 |
| e | 0 to 500 | 0 to 80 | 0 to 10 |

In another embodiment, the active phase of the catalyst corresponds to the formula:

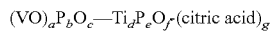

wherein the letters a, b, c, d, e, f, and g are the relative molar amounts (relative to 1.0) of VO, phosphorus, and oxygen (in the (VO)$_a$P$_b$O$_c$ component); the relative molar amounts of, titanium, phosphorus, and oxygen (in the Ti$_d$P$_e$O$_f$ component); and the relative molar amount of the oxide additive(s), respectively in the catalyst. In these embodiments, the combination of b and e may range from 10 to 30, e.g., from 23 to 26, and/or the combination of a, c, and f may range from 30 to 65, e.g., from 37 to 58. In some embodiments, the active phase of the catalyst may comprise of little or no citric acid. Preferred ranges for molar variables a, b, c, d, e, f, and g are shown in Table 2.

TABLE 2

Molar Ranges

| | Molar Range | Molar Range | Molar Range |
|---|---|---|---|
| a | 1 to 16 | 2 to 14 | 4 to 10 |
| b | 1 to 20 | 6 to 20 | 4 to 12 |
| c | 8 to 64 | 16 to 60 | 33 to 45 |
| d | 2 to 6 | 3 to 5 | 3 to 4 |
| e | 4 to 14 | 6 to 11 | 6 to 9 |
| f | 15 to 45 | 22 to 39 | 22 to 32 |
| g | 0 to 500 | 0 to 80 | 0 to 10 |

In some embodiments, the catalyst further comprises additional metals. These additional metals may function as promoters. If present, the additional metals may be selected from the group consisting of copper, molybdenum, tungsten, nickel, niobium, and combinations thereof. Other exemplary promoters that may be included in the catalyst of the invention include lithium, sodium, magnesium, aluminum, chromium, manganese, iron, cobalt, calcium, yttrium, ruthenium, silver, tin, barium, lanthanum, the rare earth metals, hafnium, tantalum, rhenium, thorium, bismuth, antimony, germanium, zirconium, uranium, cesium, zinc, and silicon and mixtures thereof. Other modifiers include boron, gallium, arsenic, sulfur, halides, Lewis acids such as BF$_3$, ZnBr$_2$, and SnCl$_4$. Exemplary processes for incorporating promoters into catalyst are described in U.S. Pat. No. 5,364,824, the entirety of which is incorporated herein by reference.

If the catalyst comprises additional metal(s) and/or metal oxides(s), the catalyst optionally may comprise additional metals and/or metal oxides in an amount from 0.001 wt % to 30 wt %, e.g., from 0.01 wt % to 5 wt % or from 0.1 wt % to 5 wt %. If present, the promoters may enable the catalyst to have a weight/weight space time yield of at least 25 grams of acrylic acid/gram catalyst-h, e.g., least 50 grams of acrylic acid/gram catalyst-h, or at least 100 grams of acrylic acid/gram catalyst-h.

In some embodiments, the catalyst is unsupported. In these cases, the catalyst may comprise a homogeneous mixture or a heterogeneous mixture. In one embodiment, the homogeneous mixture is the product of an intimate mixture of vanadium and titanium oxides, hydroxides, and phosphates resulting from preparative methods such as controlled hydrolysis of metal alkoxides or metal complexes. In other embodiments, the heterogeneous mixture is the product of a physical mixture of the vanadium and titanium phosphates. These mixtures may include formulations prepared from phosphorylating a physical mixture of preformed hydrous metal oxides. In other cases, the mixture(s) may include a mixture of preformed vanadium pyrophosphate and titanium pyrophosphate powders.

In another embodiment, the catalyst is a supported catalyst comprising a catalyst support in addition to the vanadium, titanium, and optionally phosphorous, oxygen, citric acid, and/or ethylene glycol in the amounts indicated above (wherein the molar ranges indicated are without regard to the moles of catalyst support, including any vanadium, titanium, citric acid, ethylene glycol, phosphorous or oxygen contained in the catalyst support). The total weight of the support (or modified support), based on the total weight of the catalyst, preferably is from 75 wt % to 99.9 wt %, e.g., from 78 wt % to 97 wt % or from 80 wt % to 95 wt %. The support may vary widely. In one embodiment, the support material is selected from the group consisting of silica, alumina, zirconia, titania, aluminosilicates, zeolitic materials, mixed metal oxides (including but not limited to binary oxides such as SiO$_2$—Al$_2$O$_3$, SiO$_2$—TiO$_2$, SiO$_2$—ZnO, SiO$_2$—MgO, SiO$_2$—ZrO$_2$, Al$_2$O$_3$—MgO, Al$_2$O$_3$—TiO$_2$, Al$_2$O$_3$—ZnO, TiO$_2$—MgO, TiO$_2$—ZrO$_2$, TiO$_2$—ZnO, TiO$_2$—SnO$_2$) and mixtures thereof, with silica being one preferred support. In embodiments where the catalyst comprises a titania support, the titania support may comprise a major or minor amount of rutile and/or anatase titanium dioxide. Other suitable support materials may include, for example, stable metal oxide-based supports or ceramic-based supports. Preferred supports include silicaceous supports, such as silica, silica/alumina, a Group IIA silicate such as calcium metasilicate, pyrogenic silica, high purity silica, silicon carbide, sheet silicates or clay minerals such as montmorillonite, beidellite, saponite, pillared clays, other microporous and mesoporous materials, and mixtures thereof. Other supports may include, but are not limited to, iron oxide, magnesia, steatite, magnesium oxide, carbon, graphite, high surface area graphitized carbon, activated carbons, and mixtures thereof. These listings of supports are merely exemplary and are not meant to limit the scope of the present invention.

In other embodiments, in addition to the active phase and a support, the inventive catalyst may further comprise a support modifier. A modified support, in one embodiment, relates to a support that includes a support material and a support modifier, which, for example, may adjust the chemical or physical properties of the support material such as the acidity or basicity of the support material. In embodiments that use a modified support, the support modifier is present in an amount from 0.1 wt % to 50 wt %, e.g., from 0.2 wt % to 25 wt %, from 0.5 wt % to 15 wt %, or from 1 wt % to 8 wt %, based on the total weight of the catalyst composition.

In one embodiment, the support modifier is an acidic support modifier. In some embodiments, the catalyst support is modified with an acidic support modifier. The support modifier similarly may be an acidic modifier that has a low volatility or little volatility. The acidic modifiers may be selected from the group consisting of oxides of Group IVB metals, oxides of Group VB metals, oxides of Group VIB metals, iron oxides, aluminum oxides, and mixtures thereof. In one embodiment, the acidic modifier may be selected from the group consisting of $WO_3$, $MoO_3$, $Fe_2O_3$, $Cr_2O_3$, $V_2O_5$, $MnO_2$, $CuO$, $Co_2O_3$, $Bi_2O_3$, $TiO_2$, $ZrO_2$, $Nb_2O_5$, $Ta_2O_5$, $Al_2O_3$, $B_2O_3$, $P_2O_5$, and $Sb_2O_3$.

In another embodiment, the support modifier is a basic support modifier. The presence of chemical species such as alkali and alkaline earth metals, are normally considered basic and may conventionally be considered detrimental to catalyst performance. The presence of these species, however, surprisingly and unexpectedly, may be beneficial to the catalyst performance. In some embodiments, these species may act as catalyst promoters or a necessary part of the acidic catalyst structure such in layered or sheet silicates such as montmorillonite. Without being bound by theory, it is postulated that these cations create a strong dipole with species that create acidity.

Additional modifiers that may be included in the catalyst include, for example, boron, aluminum, magnesium, zirconium, and hafnium.

In some embodiments, the support may be a high surface area support, e.g., a support having a surface area of at least 1 $m^2/g$, e.g., at least 20 $m^2/g$ or at least 50 $m^2/g$, as determined by BET measurements. The catalyst support may include pores, optionally having an average pore diameter ranging from 5 nm to 200 nm, e.g., from 5 nm to 50 nm or from 10 nm to 25 nm. The catalyst optionally has an average pore volume of from 0.05 $cm^3/g$ to 3 $cm^3/g$, e.g., from 0.05 $cm^3/g$ to 0.1 $cm^3/g$ or from 0.08 $cm^3/g$ to 0.1 $cm^3/g$, as determined by BET measurements. Preferably, at least 50% of the pore volume or surface area, e.g., at least 70% or at least 80%, is provided by pores having the diameters discussed above. Pores may be formed and/or modified by pore modification agents, which are discussed below. In another embodiment, the ratio of microporosity to macroporosity ranges from 95:5 to 85:15, e.g., from 75:25 to 70:30. Microporosity refers to pores smaller than 2 nm in diameter, and movement in micropores may be described by activated diffusion. Mesoporosity refers to pores greater than 2 nm and less than 50 nm is diameter. Flow through mesopores may be described by Knudson diffusion. Macroporosity refers to pores greater than 50 nm in diameter and flow though macropores may be described by bulk diffusion. Thus, in some embodiments, it is desirable to balance the surface area, pore size distribution, catalyst or support particle size and shape, and rates of reaction with the rate of diffusion of the reactant and products in and out of the pores to optimize catalytic performance.

As will be appreciated by those of ordinary skill in the art, the support materials, if included in the catalyst of the present invention, preferably are selected such that the catalyst system is suitably active, selective and robust under the process conditions employed for the formation of the desired product, e.g., acrylic acid or alkyl acrylate. Also, the active metals and/or pyrophosphates that are included in the catalyst of the invention may be dispersed throughout the support, coated on the outer surface of the support (egg shell) or decorated on the surface of the support. In some embodiments, in the case of macro- and meso-porous materials, the active sites may be anchored or applied to the surfaces of the pores that are distributed throughout the particle and hence are surface sites available to the reactants but are distributed throughout the support particle.

The inventive catalyst may further comprise other additives, examples of which may include: molding assistants for enhancing moldability; reinforcements for enhancing the strength of the catalyst; pore-forming or pore modification agents for formation of appropriate pores in the catalyst, and binders. Examples of these other additives include stearic acid, graphite, starch, cellulose, silica, alumina, glass fibers, silicon carbide, and silicon nitride. Preferably, these additives do not have detrimental effects on the catalytic performances, e.g., conversion and/or activity. These various additives may be added in such an amount that the physical strength of the catalyst does not readily deteriorate to such an extent that it becomes impossible to use the catalyst practically as an industrial catalyst.

In one embodiment, the inventive catalyst composition comprises a pore modification agent. A preferred type of pore modification agent is thermally stable and has a substantial vapor pressure at a temperature below 300° C., e.g., below 250° C. In one embodiment, the pore modification agent has a vapor pressure of at least 0.1 kPa, e.g., at least 0.5 kPa, at a temperature between about 150° C. and about 250° C., e.g., between about 150° C. and about 200° C.

In some embodiments, the pore modification agent has a relatively high melting point, e.g., greater than 60° C., e.g., greater than 75° C., so that it does not melt during compression of the catalyst precursor into a slug, tablet, or pellet. Preferably, the pore modification agent comprises a relatively pure material rather than a mixture. As such, lower melting components will not liquefy under compression during formation of slugs or tablets. For example, where the pore modification agent is a fatty acid, lower melting components of the fatty acid mixtures may be removed as liquids by pressing. If this phenomenon occurs during slug or tablet compression, the flow of liquid may disturb the pore structure and produce an undesirable distribution of pore volume as a function of pore diameter on the catalyst composition. In other embodiments, the pore modification agents have a significant vapor pressure at temperatures below their melting points, so that they can be removed by sublimation into a carrier gas.

For example, the pore modification agent may be a fatty acid corresponding to the formula $CH_3(CH_2)_xCOOH$ where x>8. Exemplary fatty acids include stearic acid (x=16), palmitic acid (x=14), lauric acid (x=10), myristic acid (x=12). The esters of these acids and amides or other functionalized forms of such acids, for example, stearamide ($CH_3(CH_2)_{16}CONH_2$) may also be used. Suitable esters may include methyl esters as well as glycerides such as stearin (glycerol tristearate). Mixtures of fatty acids may be used, but substantially pure acids, particularly stearic acid, are generally preferred over mixtures.

Other preferred pore modification agents include but are not limited to polynuclear organic compounds such as naphthalene, graphite, natural burnout components such as cellulose and its cellulosic derivatives, starches, natural and synthetic oligomers and polymers such as polyvinyl alcohols and polyacrylic acids and esters.

Catalyst Preparation

In one embodiment, the inventive catalyst is formed by a process comprising the step of contacting a titanium precursor, a vanadium precursor, and citric acid to form a catalyst precursor mixture. The process further comprises the step of drying, e.g., calcining, the catalyst precursor mixture to form the catalyst composition. The formation of the catalyst precursor mixture is achieved by using very little, if any, oxalic acid and lactic acid. Accordingly, the catalyst precursor mixture is substantially free of oxalic acid, lactic acid, hydrochloric acid, and/or 2-propanol. These organic compounds are traditionally utilized in the preparation of metal precursors, e.g., vanadium precursors. Without being bound by theory, it is conventionally believed that the use of oxalic acid and/or lactic acid provides for increased catalyst surface area, which in turn provides for improvements in acetic acid conversion and acrylate product selectivity and yield. As noted above, the resultant catalyst composition is substantially free of oxalic acid and lactic acid. The present invention employs citric acid and reduces or eliminates the amount of oxalic acid and lactic acid that is employed in the production of the precursor mixture and, as a result, in the catalyst composition itself. In some embodiments, in addition to the titanium precursor, the vanadium precursor, and citric acid, phosphoric acid and/or a reducing agent, e.g., ethylene glycol, may be utilized in the preparation of the catalyst precursor mixture.

In a preferred embodiment, the contacting of the above-identified components is achieved in one or more steps, e.g. two or more steps. For example, in one embodiment, the titanium precursor and phosphoric acid are contacted to form a titanium precursor mixture. The vanadium precursor may be contacted with citric acid and optionally the reducing agent to form a vanadium precursor mixture. Preferably, the formation of the vanadium precursor mixture is achieved by using very little, if any, oxalic acid and lactic acid. As a result, the vanadium precursor mixture is substantially free of oxalic acid and lactic acid.

In one embodiment of the present invention, the catalyst composition is formed by contacting, e.g., mixing, the titanium precursor mixture with the vanadium precursor mixture. The titanium pyrophosphate mixture may be prepared by contacting the titanium precursor with an alcohol, such as 2-propanol, ethanol, or i-butanol. The diluted titanium precursor may be slowly added to a colloidal silica mixture, which may be formed by combining colloidal silica, water and phosphoric acid. The vanadium mixture is separately prepared by adding a vanadium precursor to a heated citric acid mixture, which comprises citric acid, water, and optionally ethylene glycol. The vanadium mixture is heated and added to the titanium precursor mixture to form the inventive catalyst composition. Again, the formation of the precursor compositions is achieved without the use of oxalic acid and lactic acid. The process further comprises the step of dying the catalyst composition and calcining the catalyst composition as described below.

In a preferred embodiment, the titanium precursor mixture is formed by 1) contacting colloidal silica, water, and phosphoric acid to form a colloidal silica solution; 2) contacting the titanium precursor with 2-propanol to form a titanium precursor solution; 3) combining the colloidal silica solution with the titanium precursor solution to form the titanium precursor mixture. Preferably, the titanium precursor is titanium pyrophosphate, e.g., Ti(OiPr)$_4$. Preferably, the vanadium precursor is ammonium metavanadate. In one embodiment, the titanium precursor mixture is formed by contacting the titanium precursor with citric acid and optionally the reducing agent, e.g., in a manner similar to the formation of the vanadium precursor.

In one embodiment, the vanadium precursor mixture is heated to a temperature ranging from 20° C. to 100° C., e.g., from 50° C. to 100° C., before contacting the titanium precursor with the titanium precursor mixture. Preferably, the vanadium precursor mixture is heated to a temperature ranging from 50° C. to 100° C. for one hour.

In one embodiment, the drying comprises calcining at a high temperature, which yields the inventive catalyst composition. The inventive catalyst composition has a higher surface area than a corresponding catalyst composition formed without the dispersing agent.

In preferred embodiments, the titanium precursor is selected from a group consisting of Ti(OR)$_4$, L$_x$Ti(OR)$_y$ complexes, TiCl$_z$, hydrated titania sols and colloidal TiO$_2$, wherein R=methyl, ethyl, propyl, and butyl; L=acetylacetone, or similar bidentate ligands; x=1-3; y=1-3; and z=3-4. Most preferably, the titanium precursor comprises TiP$_2$O$_7$ and/or Ti(OiPr)$_4$. In one embodiment, the vanadium precursor comprises but not limited to ammonium metavanadate, vanadium pentoxide, vanadium tetraoxide, oxytrihalides, vanadium alkylcarboxylates, vanadium oxysulfate, oxyvanadium carboxylate salt, vanadium oxyacetylacetonate complex, or vanadic acid.

In some embodiments, e.g., embodiments where the catalyst is unsupported, the catalyst may be formed by a process comprising the step of dissolving at least one oxide additive and an acid, e.g., phosphoric acid, optionally in water, to form an additive solution comprising at least 0.04 wt % oxide additive, e.g., at least 0.1 wt % or at least 1 wt %. The process may further comprise the steps of adding a titanium precursor and a vanadium precursor to the additive solution to form a catalyst precursor mixture and drying the catalyst precursor mixture to form the catalyst composition. In one embodiment, the process comprises the optional step of removing at least a portion of the citric acid and/or the ethylene glycol by drying, e.g., calcining the catalyst composition.

In preferred embodiments, where the catalyst is unsupported, the catalyst composition may be formed via a process comprising the step of dissolving at least one oxide additive and an acid, e.g., phosphoric acid, in water to form an additive solution comprising at least 0.04 wt % oxide additive, e.g., at least 0.1 wt % or at least 1 wt %. The process further comprises the steps of contacting the additive solution with a titanium precursor, e.g., TiP$_2$O$_7$ or Ti(OiPr)$_4$, to form a titanium solution and contacting the titanium solution with a predetermined amount of a vanadium precursor, e.g., a soluble NH$_4$VO$_3$ solution, to form a the catalyst composition. Preferably, the process further comprises the step of drying the wet catalyst precursor to form a dried catalyst composition and optionally, further calcining the dried catalyst composition. The amounts of the titanium precursor and the vanadium precursor are determined such that the resultant dried catalyst composition has a molar ratio of vanadium to titanium greater than 0.5:1, e.g., greater than 0.75:1, greater than 1:1, or greater than 1.25:1. In one embodiment, the molar ratio of ammonium metavanadate to titanium pyrophosphate is at least 0.1:1 e.g., at least 0.5:1 or at least 1:1.

The process, in one embodiment, may further comprise calcining the dried catalyst, which, preferably, is conducted in accordance with a temperature profile. As one example, the temperature profile comprises an increasing stair step temperature profile comprising a plurality of increasing hold temperatures. The temperature increases at a rate from 1° C. to 5° C. per minute between said hold temperatures. Preferably, the hold temperatures comprise a first, second, third, and fourth hold temperature. The first hold temperature may range from 150° C. and 300° C., e.g., from 175° C. and 275° C., preferably being about 160° C. The second hold temperature may range from 250° C. and 500° C., e.g., from 300° C. and 400° C., preferably being about 250° C. The third hold temperature may range from 300° C. and 700° C., e.g., from 450° C. and 650° C., preferably being about 300° C. The fourth hold temperature may range from 400° C. and 700° C., e.g., from 450° C. and 650° C., preferably being about 450° C. Of course, other temperature profiles may be suitable. The calcination of the mixture may be done in an inert atmosphere, air or an oxygen-containing gas at the desired temperatures. Steam, a hydrocarbon or other gases or vapors may be added to the atmosphere during the calcination step or post-calcination to cause desired effects on physical and chemical surface properties as well as textural properties such as increase macroporosity.

In one preferred embodiment, the temperature profile comprises:
  i) heating the dried catalyst from room temperature to 160° C. at a rate of 10° C. per minute;
  ii) heating the dried catalyst composition at 160° C. for 2 hours;
  iii) heating the dried catalyst composition from 160° C. to 250° C. at a rate of 3° C. per minute;
  iv) heating the dried catalyst composition at 250° C. for 2 hours;
  v) heating the dried catalyst composition from 250° C. to 300° C. at a rate of 3° C. per minute;
  vi) heating the dried catalyst composition at 300° C. for 6 hours;
  vii) heating the dried catalyst composition from 300° C. to 450° C. at a rate of 3° C. per minute; and
  viii) heating the dried catalyst composition at 450° C. for 2 hours.

In another embodiment, the temperature profile comprises:
  i) contacting the catalyst composition with flowing air at a first temperature;
  ii) contacting the catalyst composition with flowing air at a second temperature greater than the first temperature; and
  iii) contacting the catalyst composition with static air at a third temperature greater than the first and second temperatures.

The first hold temperature may range from 110° C. and 210° C., e.g., from 135° C. and 185° C., preferably being about 160° C. The second hold temperature may range from 300° C. and 400° C., e.g., from 325° C. and 375° C., preferably being about 350° C. The third hold temperature may range from 400° C. and 500° C., e.g., from 425° C. and 475° C., preferably being about 450° C. In one embodiment, a first drying stage uses flowing air at 160° C. for approximately 2 hours; a second drying stage uses flowing air at 350° C. for approximately 4 hours, and a third drying stage uses static air at 450° C. for eight hours. Of course, other temperature profiles may be suitable.

In embodiments where the catalyst is supported, the catalyst compositions are formed through metal impregnation of a support (optionally modified support), although other processes such as chemical vapor deposition may also be employed.

In one embodiment, the catalysts are made by impregnating the support, with a solution of the metals or salts thereof in a suitable solvent, followed by drying and optional calcination. Solutions of the modifiers or additives may also be impregnated onto the support in a similar manner. The impregnation and drying procedure may be repeated more than once in order to achieve the desired loading of metals, modifiers, and/or other additives. In some cases, there may be competition between the modifier and the metal for active sites on the support. Accordingly, it may be desirable for the modifier to be incorporated before the metal. Multiple impregnation steps with aqueous solutions may to reduce the strength of the catalyst particles if the particles are fully dried between impregnation steps. Thus, it is preferable to allow some moisture to be retained in the catalyst between successive impregnations. In one embodiment, when using non-aqueous solutions, the modifier and/or additive are introduced first by one or more impregnations with a suitable non-aqueous solution, e.g., a solution of an alkoxide or acetate of the modifier metal in an alcohol, e.g., ethanol, followed by drying. The metal may then be incorporated by a similar procedure using a suitable solution of a metal compound.

In other embodiments, the modifier is incorporated into the composition by co-gelling or co-precipitating a compound of the modifier element with the silica, or by hydrolysis of a mixture of the modifier element halide with a silicon halide. Methods of preparing mixed oxides of silica and zirconia by sol gel processing are described by Bosman, et al., in *J Catalysis*, Vol. 148, (1994), page 660 and by Monros et al., in *J Materials Science*, Vol. 28, (1993), page 5832. Also, doping of silica spheres with boron during gelation from tetraethyl orthosilicate (TEOS) is described by Jubb and Bowen in *J Material Science*, Vol. 22, (1987), pages 1963-1970. Methods of preparing porous silicas are described in Iler R K, *The Chemistry of Silica*, (Wiley, New York, 1979), and in Brinker C J & Scherer G W *Sol-Gel Science* published by Academic Press (1990).

The catalyst composition, in some embodiments, will be used in a fixed bed reactor for forming the desired product, e.g., acrylic acid or alkyl acrylate. Thus, the catalyst is preferably formed into shaped units, e.g., spheres, granules, pellets, powders, aggregates, or extrudates, typically having maximum and minimum dimensions in the range of 1 to 25 mm, e.g., from 2 to 15 mm. Where an impregnation technique is employed, the support may be shaped prior to impregnation. Alternatively, the composition may be shaped at any suitable stage in the production of the catalyst. The catalyst also may be effective in other forms, e.g. powders or small beads and may be used in these forms. In one embodiment, the catalyst is used in a fluidized bed reactor. In this case, the catalyst may be prepared via spray drying or spray thermal decomposition. Preferably, the resultant catalyst has a particle size of greater than 300 microns, e.g., greater than 500 microns.

Production of Acrylic Acid

In other embodiments, the invention is to a process for producing unsaturated acids, e.g., acrylic acids, or esters thereof (alkyl acrylates), by contacting an alkanoic acid with an alkylenating agent, e.g., a methylenating agent, under conditions effective to produce the unsaturated acid and/or acrylate. Preferably, acetic acid is reacted with formaldehyde in the presence of the inventive catalyst composition. The alkanoic acid, or ester of an alkanoic acid, may be of the formula R'—$CH_2$—COOR, where R and R' are each, independently, hydrogen or a saturated or unsaturated alkyl or aryl group. As an example, R and R' may be a lower alkyl group containing for example 1-4 carbon atoms. In one embodiment, an alkanoic acid anhydride may be used as the source of the alkanoic acid. In one embodiment, the reaction is conducted in the presence of an alcohol, preferably the alcohol that corresponds to the desired ester, e.g., methanol. In addition to reactions used in the production of acrylic acid, the inventive catalyst, in other embodiments, may be employed to catalyze other reactions. Examples of these other reactions include, but are not limited to butane oxidation to maleic anhydride, acrolein production from formaldehyde and acetaldehyde, and methacrylic acid production from formaldehyde and propionic acid.

The acetic acid may be derived from any suitable source including natural gas, petroleum, coal, biomass, and so forth. As examples, acetic acid may be produced via methanol carbonylation, acetaldehyde oxidation, ethylene oxidation, oxidative fermentation, and anaerobic fermentation. As petroleum and natural gas prices fluctuate, becoming either more or less expensive, methods for producing acetic acid and intermediates such as methanol and carbon monoxide from alternate carbon sources have drawn increasing interest. In particular, when petroleum is relatively expensive compared to natural gas, it may become advantageous to produce acetic acid from synthesis gas ("syngas") that is derived from any available carbon source. U.S. Pat. No. 6,232,352, which is hereby incorporated by reference, for example, teaches a method of retrofitting a methanol plant for the manufacture of acetic acid. By retrofitting a methanol plant, the large capital costs associated with carbon monoxide generation for a new acetic acid plant are significantly reduced or largely eliminated. All or part of the syngas is diverted from the methanol synthesis loop and supplied to a separator unit to recover carbon monoxide and hydrogen, which are then used to produce acetic acid.

Methanol carbonylation processes suitable for production of acetic acid are described in U.S. Pat. Nos. 7,208,624; 7,115,772; 7,005,541; 6,657,078; 6,627,770; 6,143,930; 5,599,976; 5,144,068; 5,026,908; 5,001,259; and 4,994,608, all of which are hereby incorporated by reference.

U.S. Pat. No. RE 35,377, which is hereby incorporated by reference, provides a method for the production of methanol by conversion of carbonaceous materials such as oil, coal, natural gas and biomass materials. The process includes hydrogasification of solid and/or liquid carbonaceous materials to obtain a process gas which is steam pyrolized with additional natural gas to form syngas. The syngas is converted to methanol which may be carbonylated to acetic acid. U.S. Pat. No. 5,821,111, which discloses a process for converting waste biomass through gasification into syngas, as well as U.S. Pat. No. 6,685,754 are hereby incorporated by reference.

In one optional embodiment, the acetic acid that is utilized in the condensation reaction comprises acetic acid and may also comprise other carboxylic acids, e.g., propionic acid, esters, and anhydrides, as well as acetaldehyde and acetone. In one embodiment, the acetic acid fed to the hydrogenation reaction comprises propionic acid. For example the propionic acid in the acetic acid feed stream may range from 0.001 wt % to 15 wt %, e.g., from 0.001 wt % to 0.11 wt %, from 0.125 wt % to 12.5 wt %, from 1.25 wt % to 11.25, or from 3.75 wt % to 8.75 wt %. Thus, the acetic acid feed stream may be a cruder acetic acid feed stream, e.g., a less-refined acetic acid feed stream.

As used herein, "alkylenating agent" means an aldehyde or precursor to an aldehyde suitable for reacting with the alkanoic acid, e.g., acetic acid, in an aldol condensation reaction to form an unsaturated acid, e.g., acrylic acid, or an alkyl acrylate. In preferred embodiments, the alkylenating agent comprises a methylenating agent such as formaldehyde, which preferably is capable of adding a methylene group ($=CH_2$) to the organic acid. Other alkylenating agents may include, for example, acetaldehyde, propanal, and butanal.

The alkylenating agent, e.g., formaldehyde, may be added from any suitable source. Exemplary sources may include, for example, aqueous formaldehyde solutions, anhydrous formaldehyde derived from a formaldehyde drying procedure, trioxane, diether of methylene glycol, and paraformaldehyde. In a preferred embodiment, the formaldehyde is produced via a formox unit, which reacts methanol and oxygen to yield the formaldehyde.

In other embodiments, the alkylenating agent is a compound that is a source of formaldehyde. Where forms of formaldehyde that are not as freely or weakly complexed are used, the formaldehyde will form in situ in the condensation reactor or in a separate reactor prior to the condensation reactor. Thus for example, trioxane may be decomposed over an inert material or in an empty tube at temperatures over 350° C. or over an acid catalyst at over 100° C. to form the formaldehyde.

In one embodiment, the alkylenating agent corresponds to Formula I.

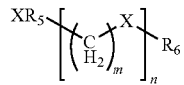

In this formula, $R_5$ and $R_6$ may be independently selected from $C_1$-$C_{12}$ hydrocarbons, preferably, $C_1$-$C_{12}$ alkyl, alkenyl or aryl, or hydrogen. Preferably, $R_5$ and $R_6$ are independently $C_1$-$C_6$ alkyl or hydrogen, with methyl and/or hydrogen being most preferred. X may be either oxygen or sulfur, preferably oxygen; and n is an integer from 1 to 10, preferably 1 to 3. In some embodiments, m is 1 or 2, preferably 1.

In one embodiment, the compound of formula I may be the product of an equilibrium reaction between formaldehyde and methanol in the presence of water. In such a case, the compound of formula I may be a suitable formaldehyde source. In one embodiment, the formaldehyde source includes any equilibrium composition. Examples of formaldehyde sources include but are not restricted to methylal (1,1 dimethoxymethane); polyoxymethylenes —$(CH_2$—$O)_i$— wherein i is from 1 to 100; formalin; and other equilibrium compositions such as a mixture of formaldehyde, methanol, and methyl propionate. In one embodiment, the source of formaldehyde is selected from the group consisting of 1,1 dimethoxymethane; higher formulas of formaldehyde and methanol; and $CH_3$—O—$(CH_2$—$O)_i$—$CH_3$ where i is 2.

The alkylenating agent may be used with or without an organic or inorganic solvent.

The term "formalin," refers to a mixture of formaldehyde, methanol, and water. In one embodiment, formalin comprises from 25 wt % to 65 wt % formaldehyde; from 0.01 wt % to 25 wt % methanol; and from 25 wt % to 70 wt % water. In cases where a mixture of formaldehyde, methanol, and methyl propionate is used, the mixture comprises less than 10 wt % water, e.g., less than 5 wt % or less than 1 wt %.

In some embodiments, the condensation reaction may achieve favorable conversion of acetic acid and favorable selectivity and productivity to acrylates. For purposes of the present invention, the term "conversion" refers to the amount of acetic acid in the feed that is converted to a compound other than acetic acid. Conversion is expressed as a mole percentage based on acetic acid in the feed. The conversion of acetic acid may be at least 11 mol. %, e.g., at least 20 mol. %, at least 40 mol. %, or at least 50 mol. %. In another embodiment, the reaction may be conducted wherein the molar ratio of acetic acid to alkylenating agent is at least 0.55:1, e.g., at least 1:1.

Selectivity is expressed as the ratio of the amount of carbon in the desired product(s) and the amount of carbon in the total products. This ratio may be multiplied by 100 to arrive at the selectivity. Preferably, the catalyst selectivity to acrylates, e.g., acrylic acid and methyl acrylate, is at least 40 mol. %, e.g., at least 50 mol. %, at least 60 mol. %, or at least 70 mol. %. In some embodiments, the selectivity to acrylic acid is at least 30 mol. %, e.g., at least 40 mol. %, or at least 50 mol. %; and/or the selectivity to methyl acrylate is at least 10 mol. %, e.g., at least 15 mol. %, or at least 20 mol. %.

The term "productivity," as used herein, refers to the grams of a specified product, e.g., acrylates, formed during the condensation based on the liters of catalyst used per hour. A productivity of at least 20 grams of acrylates per liter catalyst per hour, e.g., at least 40 grams of acrylates per liter catalyst per hour or at least 100 grams of acrylates per liter catalyst per hour, is preferred. In terms of ranges, the productivity preferably is from 20 to 500 grams of acrylates per liter catalyst per hour, e.g., from 20 to 200 grams of acrylates per kilogram catalyst per hour or from 40 to 140 grams of acrylates per kilogram catalyst per hour.

As noted above, the inventive catalyst compositions provide for high conversions of acetic acid. Advantageously, these high conversions are achieved while maintaining or in some cases improving selectivity to the desired acrylates, e.g., acrylic acid and/or methyl acrylate. As a result, acrylate productivity is improved, as compared to conventional productivity with conventional catalysts, which are prepared using significant portions of oxalic acid and lactic acid and little if any citric acid.

The acetic acid conversion, in some embodiments, may vary depending upon the reaction temperature. In one embodiment, for example, when the reaction temperature is approximately 340° C., the acetic acid conversion is at least 11%, e.g., at least 15% or at least 25%. The selectivity to acrylates is maintained at, for example, at least 60.6%, e.g., at least 65%, at least 75% or at least 90%. Accordingly, the productivity, e.g., the space time yield, of acrylates is at least 30.4 grams per liter catalyst per hour, e.g., at least 35 grams per liter or at least 55 grams per liter, when the reaction temperature is approximately 340° C.

In another embodiment where the reaction temperature is approximately 350° C., the acetic acid conversion is at least 27.8%, e.g., at least 30% or at least 35%. The selectivity to acrylates is maintained at, for example, at least 65%, e.g., at least 68%, or at least 72%. Accordingly, the productivity, e.g., the space time yield, of acrylates is at least 56.8 grams per liter of catalyst per hour, e.g., at least 70 grams per liter of catalyst per hour or at least 85 grams per liter of catalyst per hour, when the reaction temperature is approximately 355° C.

In another embodiment where the reaction temperature is approximately 370° C., the acetic acid conversion is at least 37.9%, e.g., at least 40% or at least 45%. The selectivity to acrylates is maintained at, for example, at least 66.3%, e.g., at least 70%, or at least 75%. Accordingly, the productivity, e.g., the space time yield, of acrylates is at least 96.1 grams per liter of catalyst per hour, e.g., at least 110 grams per liter of catalyst per hour or at least 120 grams per liter of catalyst per hour, when the reaction temperature is approximately 370° C.

The alkanoic acid or ester thereof and alkylenating agent may be fed independently or after prior mixing to a reactor containing the catalyst. The reactor may be any suitable reactor. Preferably, the reactor is a fixed bed reactor, but other reactors such as a continuous stirred tank reactor or a fluidized bed reactor, may be used.

In some embodiments, the alkanoic acid, e.g., acetic acid, and the alkylenating agent, e.g., formaldehyde, are fed to the reactor at a molar ratio of at least 0.10:1, e.g., at least 0.75:1 or at least 1:1. In terms of ranges the molar ratio of alkanoic acid to alkylenating agent may range from 0.10:1 to 10:1 or from 0.75:1 to 5:1. In some embodiments, the reaction of the alkanoic acid and the alkylenating agent is conducted with a stoichiometric excess of alkanoic acid. In these instances, acrylate selectivity may be improved. As an example the acrylate selectivity may be at least 10% higher than a selectivity achieved when the reaction is conducted with an excess of alkylenating agent, e.g., at least 20% higher or at least 30% higher. In other embodiments, the reaction of the alkanoic acid and the alkylenating agent is conducted with a stoichiometric excess of alkylenating agent.

The aldol condensation reaction may be conducted at a temperature of at least 250° C., e.g., at least 300° C., or at least 350° C. In terms of ranges, the reaction temperature may range from 200° C. to 500° C., e.g., from 250° C. to 400° C., or from 250° C. to 350° C. Residence time in the reactor may range from 1 second to 200 seconds, e.g., from 1 second to 100 seconds. Reaction pressure is not particularly limited, and the reaction is typically performed near atmospheric pressure. In one embodiment, the reaction may be conducted at a pressure ranging from 0 kPa to 4100 kPa, e.g., from 3 kPa to 345 kPa, or from 6 kPa to 103 kPa.

Water may be present in amounts up to 60 wt %, by weight of the reaction mixture, e.g., up to 50 wt % or up to 40 wt %. Water, however, is preferably reduced due to its negative effect on process rates and separation costs.

In one embodiment, an inert or reactive gas is supplied to the reactant stream. Examples of inert gases include, but are not limited to, nitrogen, helium, argon, and methane. Examples of reactive gases or vapors include, but are not limited to, oxygen, carbon oxides, sulfur oxides, and alkyl halides. When reactive gases such as oxygen are added to the reactor, these gases, in some embodiments, may be added in stages throughout the catalyst bed at desired levels as well as feeding with the other feed components at the beginning of the reactors.

In one embodiment, the unreacted components such as the carboxylic acid and formaldehyde as well as the inert or reactive gases that remain are recycled to the reactor after sufficient separation from the desired product.

When the desired product is an unsaturated ester made by reacting an ester of an alkanoic acid ester with formaldehyde, the alcohol corresponding to the ester may also be fed to the reactor either with or separately to the other components. For example, when methyl acrylate is desired, methanol may be fed to the reactor. The alcohol, amongst other effects, reduces the quantity of acids leaving the reactor. It is not necessary that the alcohol is added at the beginning of the reactor and it may for instance be added in the middle or near the back, in order to effect the conversion of acids such as propionic acid, methacrylic acid to their respective esters without depressing catalyst activity.

EXAMPLES

Catalyst Preparation

Example 1

2.0 grams 40% colloidal silica was mixed with 50 ml deionized water and 11.69 grams of phosphoric acid. 10.98 grams $Ti(OiPr)_4$ was slowly added to 10 ml of 2-propanol. The diluted $Ti(OiPr)_4$ solution was slowly added to the colloidal silica mixture. This suspension was stirred for one hour at room temperature. Separately, 3.69 grams of citric acid was added to a solution of 12 ml ethylene glycol, 5 ml water. The citric acid mixture was heated to 85° C.; when the solution reached approximately 50° C., 2.26 grams solid ammonium metavanadate was slowly added with constant stirring. The citric acid/ammonium metavanadate mixture was stirred at 85° C. for one hour. The hot solution was added to the suspension of Ti(OiPr)$_4$ and rinsed with 5 ml of deionized water. The solution was stirred at room temperature for 30 minutes. The resultant material was dried with rotary evaporator set at 95° C. The tacky solid was further dried at 120° C. overnight to a solid consistency. The solid was calcined using the following profile:

i) drying with flowing air at 160° C. for 2 hours;
ii) drying with flowing air at 350° C. for 4 hours;
iii) drying under static air at 450° C. for eight hours.

Example 2

2.0 grams 40% colloidal silica was mixed with 50 ml deionized water and 11.69 grams of phosphoric acid. 10.98 grams Ti(OiPr)$_4$ was slowly added to 10 ml of 2-propanol. The diluted Ti(OiPr)$_4$ solution was slowly added to the colloidal silica mixture. This suspension was stirred for one hour at room temperature. Separately, 3.69 grams of citric acid was added to a solution of 17 ml water. The citric acid mixture was heated to 85° C.; when the solution reached approximately 50° C., 2.26 grams solid ammonium metavanadate was slowly added with constant stirring. The citric acid/ammonium metavanadate mixture was stirred at 85° C. for one hour. The hot solution was added to the suspension of Ti(OiPr)$_4$ and rinsed with 5 ml of deionized water. The solution was stirred at room temperature for 30 minutes. The resultant material was dried as in Example 2.

Comparative Example A

The procedure of Example 1 was repeated, with the exception of the formation of the vanadium precursor. In Comparative Example A oxalic acid dehydrate was added to a solution of 12 ml ethylene glycol and 5 ml water and citric acid was not used.

Comparative Example B

The procedure of Example 1 was repeated, with the exception of the formation of the vanadium precursor. In Comparative Example A oxalic acid dehydrate was added to a solution of 17 ml water and citric acid was not used.

The surface area and pore size of the catalysts of the invention and of the comparative example were measured. The results are shown in Table 3.

TABLE 3

| Catalyst Sample | Dispersing Agent Mixture | Surface area (m$^2$/g) | Average Pore Size (nm) |
| --- | --- | --- | --- |
| Example A | Oxalic acid and ethylene glycol | 22.6* | 17.4* |
| Example B | Oxalic acid | 0.6 | 11.9 |
| Example 1 | Citric acid and ethylene glycol | 20.7 | 16.0 |
| Example 2 | Citric acid | 13.5 | 15.7 |

*Data point is an average of two experimental results.

As shown in Table 3, the use of oxalic acid alone as a solvent for the vanadium precursor composition resulted in a catalyst composition having a surface area of 0.6 m$^2$/g and average pore size of 11.9 nm. When the citric acid replaces at least a portion of the oxalic acid, surface area is surprisingly and unexpectedly improved to 13.5 m$^2$/g. Also, the combination of citric acid an ethylene glycol surprisingly and unexpectedly yielded a catalyst composition having an average pore size that is less than the 17.4 nm. As shown below, the catalyst compositions of the invention with increased surface area and decreased average pore size, beneficially, provide for increased acetic acid conversions, while maintaining selectivity to the desired acrylates. As a result, acrylate space time yield is increased over comparable catalysts having the same components in the active phase, but different surface areas and average pore sizes.

A reaction feed comprising acetic acid (9.1%), formaldehyde (17.3%), methanol (6.7%), water (38%), oxygen (4.06%), and nitrogen (24.8%) was passed through a fixed bed reactor comprising the catalysts from Example 1, Example 2, and Comparative Example A. The reaction was conducted at three temperatures, 340° C., 355° C., and 370° C. Multiple runs at these temperatures were performed. Acrylic acid and methyl acrylate (collectively, "acrylates") were produced. The respective runs were averaged and the average conversions, selectivities, and space time yields are shown in Table 4.

TABLE 4

Acrylate Product Conversions and Selectivities

| Reaction Temperature | Catalyst Sample | Acetic Acid Conv. | Acrylic Acid Sel. | Acrylic Acid STY, g/liter of catalyst/hr | Acrylate Sel. | Acrylate STY, g/liter of catalyst/hr |
| --- | --- | --- | --- | --- | --- | --- |
| 340° C. | Ex. 1 | 22.9 | 51.0 | 43.0 | 71.2 | 57.2 |
| 340° C. | Ex. 2 | 18.2 | 46.3 | 31.8 | 63.6 | 42.4 |
| 340° C. | Comp. A | 10.5 | 45.0 | 20.4 | 63.2 | 27.8 |
| 355° C. | Ex. 1 | 33.0 | 54.0 | 67.9 | 71.6 | 87.8 |
| 355° C. | Ex. 2 | 31.7 | 52.7 | 63.9 | 66.9 | 79.3 |
| 355° C. | Comp. A | 19.8 | 46.8 | 38.1 | 63.5 | 50.2 |
| 370° C. | Ex. 1 | 47.8 | 57.9 | 103.3 | 72.3 | 126.3 |
| 370° C. | Ex. 2 | 50.8 | 55.9 | 105.4 | 67.1 | 124.3 |
| 370° C. | Comp. A | 36.0 | 53.7 | 72.4 | 68.3 | 90.1 |

As shown in Table 4, the reduction or elimination of oxalic acid and lactic acid in catalyst preparation and/or the replacement thereof with citric acid not only maintains acetic acid conversion, but surprisingly and unexpectedly provides for significant improvements in acetic acid conversion. Also, as shown in Table 4, the improved conversions are surprisingly and unexpectedly achieved while selectivities to acrylic acid and/or acrylates are maintained, or in most cases, improved. As a result of these improvements in conversion and selectivity, higher productivities, e.g., space time yields, are shown at all three temperatures.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

We claim:

1. A catalyst composition comprising an active phase, the active phase comprising:
    vanadium;
    titanium; and
    from 0.01 wt % to 10 wt % citric acid,
    wherein the catalyst composition is substantially free of oxalic acid and lactic acid.

2. The catalyst composition of claim 1, further comprising ethylene glycol.

3. The catalyst composition of claim 1, wherein a molar ratio of citric acid to the combination of vanadium and titanium in an active phase of the catalyst ranges from 0.1:10 to 10:1.

4. The catalyst composition of claim 1, wherein a molar ratio of citric acid to vanadium in an active phase of the catalyst composition ranges from 0.1:1.0 to 10:1.

5. The catalyst composition of claim 1, wherein a molar ratio of citric acid to titanium in an active phase of the catalyst composition ranges from 0.0:1.0 to 10:1.

6. The catalyst composition of claim 1, wherein a molar ratio of vanadium to titanium in an active phase of the catalyst composition is greater than 0.5:1.

7. The catalyst composition of claim 1, wherein an active phase of the catalyst composition comprises from 5 wt % to 40 wt % titanium.

8. The catalyst composition of claim 1, wherein an active phase of the catalyst composition comprises from 1 wt % to 40 wt % vanadium.

9. The catalyst composition of claim 1, wherein the catalyst composition further comprises:
    from 15 wt % to 45 wt % phosphorus; and
    from 30 wt % to 75 wt % oxygen.

10. The catalyst composition of claim 1, wherein the catalyst composition further comprises a support.

11. The catalyst composition of claim 10, wherein the support is selected from the group consisting of silica, alumina, zirconia, titania, aluminosilicates, zeolitic materials, and mixtures thereof.

12. A catalyst composition, comprising:
    vanadium;
    titanium;
    wherein the catalyst composition comprises a plurality of pores, the plurality of pores having an average pore diameter less than 17.4 nm; and
    wherein the catalyst composition has a surface area of at least 13.5 m$^2$/g.

13. The catalyst composition of claim 12, further comprising ethylene glycol and from 0.01 wt % to 10 wt % citric acid.

14. The catalyst composition of claim 12, wherein the catalyst composition is substantially free of oxalic acid and lactic acid.

15. A process for producing a catalyst composition, comprising:
    (a) contacting a titanium precursor, a vanadium precursor, phosphoric acid, citric acid, and optionally a reducing agent to form a catalyst precursor mixture, wherein the catalyst precursor mixture is substantially free of oxalic acid and lactic acid; and
    (b) drying the catalyst precursor mixture to form a catalyst composition comprising titanium and vanadium, wherein the catalyst composition is substantially free of oxalic acid and lactic acid.

16. The process of claim 15, wherein the catalyst composition further comprises citric acid.

17. The process of claim 15, wherein the catalyst precursor mixture comprises the reducing agent.

18. The process of claim 17, wherein the reducing agent is ethylene glycol.

19. The process of claim 15, wherein the catalyst composition comprises a plurality of pores, the plurality of pores having an average pore diameter less than 17.4 nm.

20. The process of claim 15, wherein the catalyst composition has a surface area of at least 13.5 m$^2$/g.

21. The process of claim 15, wherein step (a) comprises:
    contacting the titanium precursor and phosphoric acid, to form a titanium precursor mixture;
    contacting the vanadium precursor with citric acid and optionally the reducing agent, to form a vanadium precursor mixture, wherein the vanadium precursor mixture is substantially free of oxalic acid and lactic acid; and
    contacting the titanium precursor mixture with the vanadium precursor mixture to form the catalyst precursor mixture.

22. The process of claim 15, wherein the formation of the titanium precursor mixture comprises:
    contacting colloidal silica, water, and phosphoric acid to form a colloidal silica solution;
    contacting the titanium precursor with 2-propanol to form a titanium precursor solution;
    combining the colloidal silica solution with the titanium precursor solution to form the titanium precursor mixture.

23. The process of claim 22, further wherein the titanium precursor is Ti(OiPr)$_4$.

24. The process of claim 15, further comprising heating the vanadium precursor mixture to a temperature ranging from 20° C. to 100° C. before contacting the titanium precursor with the titanium precursor mixture.

25. The process of claim 15, further comprising heating the vanadium precursor mixture to a temperature ranging from 50° C. to 100° C. for one hour.

26. The process of claim 15, wherein the titanium precursor is selected from a group consisting of $Ti(OR)_4$, $L_xTi(OR)_y$, complexes, $TiCl_z$, hydrated titania sols and colloidal $TiO_2$, wherein
R=methyl, ethyl, propyl, isopropyl, and butyl;
L=bidientate ligands;
x=1-3;
y=1-3; and
z=3-4.

27. The process of claim 15, wherein the titanium precursor is $Ti(OiPr)_4$.

28. The process of claim 15, wherein the vanadium precursor comprises ammonium metavanadate.

29. The process of claim 15, wherein step (b) comprises calcining the catalyst composition.

30. The process of claim 29, wherein the calcining comprises:
contacting the catalyst composition with flowing air at a first temperature;
contacting the catalyst composition with flowing air at a second temperature greater than the first temperature; and
contacting the catalyst composition with static air at a third temperature greater than the first and second temperature.

31. The process of claim 30, wherein the first temperature ranges from 110° C. to 210° C., the second temperature ranges from 300° C. to 400° C. and the third temperature ranges from 400° C. to 500° C.

32. A catalyst composition produced by the process of claim 15.

33. A process for producing a catalyst composition, comprising:
(a) contacting a titanium precursor and phosphoric acid to form a titanium precursor mixture;
(b) contacting a vanadium precursor with a citric acid and optionally a reducing agent to form a vanadium precursor mixture, wherein the vanadium precursor mixture is substantially free of oxalic acid and lactic acid;
(c) contacting the titanium precursor mixture with the vanadium mixture to form a catalyst composition comprising titanium, vanadium, citric acid, wherein the catalyst composition mixture is substantially free of oxalic acid and lactic acid; and
(d) optionally removing at least a portion of the citric acid by calcining the catalyst composition.

34. A process for producing acrylic acid comprising the steps of:
contacting acetic acid and an alkylenating agent over a catalyst composition to produce acrylic acid and/or acrylate,
wherein the catalyst composition comprises vanadium, titanium, ethylene glycol, and optionally citric acid,
wherein the catalyst composition is substantially free of oxalic acid and lactic acid.

35. The process of claim 34, wherein the catalyst composition further comprises ethylene glycol.

36. The process of claim 34, wherein the alkylenating agent comprises formaldehyde.

37. The process of claim 34, wherein the overall acetic acid conversion is at least 11% at 340° C.

38. The process of claim 34, wherein the over acetic acid conversion is at least 27.8% at 355° C.

39. The process of claim 34, wherein the over acetic acid conversion is at least 37.9% at 370° C.

40. The process of claim 34, wherein the space time yield of the combination of acrylic acid and acrylate is at least 30.4 grams/liter of catalyst/hour at 340° C.

41. The process of claim 34, wherein the space time yield of the combination of acrylic acid and acrylate is at least 56.8 grams/liter of catalyst/hour at 355° C.

42. The process of claim 34, wherein the space time yield of the combination of acrylic acid and acrylate is at least 96.1 grams/liter of catalyst/hour at 370° C.

43. A process for producing acrylic acid comprising the steps of:
(a) contacting a titanium precursor, a vanadium precursor, phosphoric acid, citric acid, and a reducing agent to form a catalyst precursor mixture, wherein the catalyst precursor mixture is substantially free of oxalic acid and lactic acid; and
(b) drying the catalyst precursor mixture to form a catalyst composition comprising titanium, vanadium, reducing agent, and optionally citric acid, wherein the catalyst composition is substantially free of oxalic acid and lactic acid; and
(c) contacting acetic acid and an alkylenating agent over the catalyst composition to produce acrylic acid and/or acrylate.

* * * * *